United States Patent [19]

Tabata et al.

[11] Patent Number: 5,233,100
[45] Date of Patent: Aug. 3, 1993

[54] PROCESS FOR PRODUCING ALCOHOL

[75] Inventors: Osamu Tabata; Atsuhito Mori; Takahiro Kawakami; Kunizo Hashiba; Kiyoshi Tsukada, all of Wakayama, Japan

[73] Assignee: Kao Corporation, Tokyo, Japan

[21] Appl. No.: 813,918

[22] Filed: Dec. 27, 1991

[30] Foreign Application Priority Data

Dec. 27, 1990 [JP] Japan .................................. 2-408223
Sep. 11, 1991 [JP] Japan .................................. 3-231705

[51] Int. Cl.$^5$ ................... C07C 29/149; C07C 31/125
[52] U.S. Cl. .................................... 568/885; 568/814; 568/836; 568/853; 568/864
[58] Field of Search ............... 568/885, 864, 836, 814, 568/853

[56] References Cited

U.S. PATENT DOCUMENTS 4,982,020  1/1991  Carduck et al. .................... 568/885
5,043,485  8/1991  Fleckenstein et al. .............. 568/885

FOREIGN PATENT DOCUMENTS 0143634  6/1985  European Pat. Off. .
2613226  9/1977  Fed. Rep. of Germany .
64642  11/1955  France .

OTHER PUBLICATIONS

Derwent Abstract of SU-A 445261.

Primary Examiner—Joseph E. Evans
Attorney, Agent, or Firm—Sughrue, Mion, Zinn, Macpeak & Seas

[57] ABSTRACT

A process for producing an alcohol from a fatty acid ester, a fatty acid triglyceride or a fatty acid by continuously catalytically reducing the starting material in the presence of a hydrogenation catalyst is disclosed. In the process of the present invention, two reactors (i.e., the main reactor located upstream and the after reactor located downstream) being located in series are employed. In the process of the present invention, two reactors are employed and the temperatures thereof are individually controlled, whereby the conversion ratio is elevated while suppressing the formation of hydrocarbon and aldehyde by-products. Thus, an alcohol of extremely high quality and high purity can be produced. Further, the process of the present invention makes it possible to omit any post-treatment for eliminating the by-products. Furthermore, the active life of the hydrogenation catalyst can be remarkably prolonged by using three reactors (i.e., the guard reactor, the main reactor and the after reactor).

15 Claims, No Drawings

PROCESS FOR PRODUCING ALCOHOL

FIELD OF THE INVENTION

This invention relates to a novel process for the continuous catalytic reduction of a fatty acid ester, a fatty acid triglyceride or a fatty acid in the presence of a hydrogenation catalyst.

BACKGROUND OF THE INVENTION

A conventional method for producing a fatty alcohol comprises catalytically reducing a starting material selected from among natural fats and oils, fatty acids and fatty acid esters to thereby obtain a fatty alcohol. This reaction is to be performed in the presence of a hydrogenation catalyst under a pressure of 250 to 300 bar at a temperature of 200° C. or above under an excess hydrogen atmosphere.

In the method disclosed in West Germany Patent DE-2613226, a starting material (coconut oil methyl ester) is preliminarily gasified and then an alcohol is produced using two fixed bed reactors connected in series.

Since the reduction of a fatty acid ester, a fatty acid triglyceride or a fatty acid is an exothermic reaction, when an alcohol is produced by catalytically reducing these starting materials in a fixed bed reactor, the reaction has been carried out under apparently isothermal conditions with liberating the heat generated during the course of the reaction in the reactor in order to improve qualities of the alcohols thus produced, as disclosed in JP-A-64-47725 (corresponding to U.S. Pat. No. 5,043,485), JP-A-64-47726 (corresponding to EP-A-0300346), JP-A-63-39829 (corresponding to U.S. Pat. No. 4,942,020) and JP-A-1-275542 (corresponding to U.S. Pat. No. 4,942,266) (the term "JP-A" as used herein means an "unexamined published Japanese patent application") and U.S. Pat. No. 4,855,273 and U.S. Pat. No. 4,935,556.

When a hydrogenation reaction is effected at a usual reaction temperature in a method for producing a fatty alcohol, the reaction would excessively proceed and thus by-products (for example, hydrocarbons, aldehydes) are formed. Since the reduction of a fatty acid ester, a fatty acid triglyceride or a fatty acid is an exothermic reaction, during the reduction of these starting materials, the temperature in a reactor increases to more than that of the reactor inlet. In this case, therefore, it is difficult to reduce the amount of these by-products by controlling the reaction temperature in a single reactor. In the above-mentioned JP-A-64-47725 (corresponding to U.S. Pat. No. 5,043,485), JP-A-64-47726 (corresponding to EP-A-0300346) and JP-A-1-275542 (corresponding to U.S. Pat. No. 4,942,266) and U.S. Pat. No. 4,855,273 and U.S. Pat. No. 4,935,556, the reaction is performed in a single reactor under approximately isothermal conditions. Accordingly, the amount of the by-products can hardly be reduced.

Further, it is required to eliminate hydrocarbons or aldehydes formed by the excessive reaction, since the qualities of the alcohol are deteriorated by these by-products. The boiling point ranges of the hydrocarbons overlap these of short-chain alcohols and thus the starting material must be fractionated by, for example, distillation prior to the reaction.

On the other hand, the aldehydes are converted into fatty alcohols of the corresponding chain length by treating with a chemical, i.e., a reducing agent.

However, these treatments are disadvantageous in that they make the procedure complicated and cause an increase in the production cost.

In DE-2613226, the starting material for producing an alcohol is gasified and the reaction is performed by using two reactors. However the gas phase reaction makes it further difficult to control the temperatures in the reactors and an amount of hydrocarbon by-products, in particular, formed during the reaction increases. In addition, the reaction temperature in each reactor is not specified in this patent and, therefore, the object of the use of the two reactors is unclear.

SUMMARY OF THE INVENTION

It is an object of the present invention to produce a fatty alcohol having excellent qualities and a high purity by using two or more reactors without performing any post-treatment of the product.

The present inventors found that, by using two or more reactors in a process for producing a fatty alcohol by catalytically reducing a fatty acid ester, a fatty acid triglyceride or a fatty acid in the presence of a hydrogenation catalyst, a fatty alcohol having excellent qualities and a high purity can be obtained without need of any post-treatment, thus completing the present invention.

Accordingly, the present invention provides a process for producing an alcohol which comprises:

continuously feeding a starting material selected from a fatty acid ester, a fatty acid triglyceride and a fatty acid and hydrogen into two reactors which are located in series and in each of which a hydrogenation catalyst is contained, hydrogen being fed at about 20 to about 300 bar and the starting material being fed in such a manner as to give a molar ratio of hydrogen to the fatty acid group of the starting material of from about 5:1 to about 500:1;

reacting the starting material and hydrogen in the presence of the hydrogenation catalysts in the two reactors; and then recovering the alcohol, wherein the two reactors comprise a main reactor being located at the upstream and an after reactor being located at the downstream, a temperature of the main reactor is controlled so as to give a conversion ratio of the starting material at the outlet of the main reactor of 50 to 100% and a hydrocarbon by-product concentration of 0.5% by weight or less in the reaction products at the outlet of the main reactor, and a temperature of the after reactor is controlled so as to elevate a conversion ratio of the starting material at the outlet of the main reactor and/or to give an aldehyde concentration in the reaction products at the outlet of the after reactor of 30 ppm or below. A guard reactor is further employed in the process, if required, in order to eliminate sulfur compounds contained in the starting material.

DETAILED DESCRIPTION OF THE INVENTION

As the reactors to be used in the present invention, any reactors useful for producing fatty alcohols may be employed. Examples therefor include a fluidized bed reactor, including a three phase (i.e., gas-liquid-solid) fluidized bed reactor and a three phase slurry bubble reactor, wherein a catalytic reduction is performed by fluidizing a catalyst with a fluid; a moving bed reactor, wherein a catalytic reduction is performed by feeding a fluid while the whole catalytic layer gradually falls due to the gravity; a fixed bed reactor wherein a catalytic reduction is performed by fixing a catalyst and feeding a fluid thereto and the like.

As the fluidized bed reactor, the moving bed reactor and the fixed bed reactor, as conventionally used in the art may be used in the present invention. Details of the fluidized bed reactor are disclosed, for example, in G. Diecklmann and H. J. Heinz, *THE BASICS OF INDUSTRIAL OLEOCHEMISTRY*, published by Peter Promp GmbH, pages 91–102 (1988); details of the moving bed reactor are disclosed, for example, in W. C. van Zijill Langhout et al. *OIL & GAS JOURNAL*, Dec., pages 120–126 (1980); and details of the fixed bed reactor are disclosed, for example, in DE-2613226.

In the process of the present invention, it is preferred that both of the main and after reactors or all of the main, after and guard reactors are the reactors of the same type, in view of the workability of the process, the simplicity of the system and the like.

In the process of the present invention, the main reactor contributes to convert many parts or all of the starting material and the after reactor contributes to lower the aldehyde by-products concentration and to convert the remaining starting material if it remains.

In the process of the present invention, both the main and after reactors include those comprising a single bed reactor and those of which plural bed reactors are provided in series as a multistage.

The catalyst useful in the process of the present invention may be a known one commonly used in hydrogenation such as a Cu-Cr catalyst as disclosed, for example, in *Industrial and Engineering Chemistry*, vol. 26, page 878 (1936); Cu-Zn catalyst as disclosed, for example, in JP-A-63-141937, JP-A-2-36135 and JP-A-2-157044; Cu-Fe-Al catalyst as disclosed, for example, in JP-B-58-50775 (the term "JP-B" as used herein means "examined Japanese Patent Publication"); and Cu-Zn-Ti catalyst as disclosed, for example, in JP-A-1-305042. The catalyst may be used in the form of either powders, granules or tablets, depending on the type of the employed reactors.

As the starting fatty acid ester, straight-chain or branched and saturated or unsaturated fatty acid esters having one or more alcohol residues having one or more carbon atoms. Further, alicyclic carboxylic esters and aromatic carboxylic esters may be used therefor.

Examples of the alcohol residue include residues of straight- or branched-chain alcohols having 1 to 20 carbon atoms such as methanol, ethanol, 1-propanol, 2-propanol, 1-butanol, 2-butanol, 2-ethylhexanol, 2,2-dimethyl-1,3-propanediol, ethylene glycol, propylene glycol, 1,4-butanediol, 1,6-hexanediol, 1,10-decanediol, cyclohexanol, benzyl alcohol, diethylene glycol, glycerol, trimethylolpropane and the like.

Examples of the fatty acid esters and carboxylates include formates, acetates, caproates, caprylates, undecenoates, laurates, myristates, palmitates, stearates, isostearates, oleates, oxalates, maleates, adipates, sebacates, cyclohexanecarboxylates, benzoates, phthalates and the like, though the present invention is not restricted thereby.

Examples of the starting fatty acid triglyceride include coconut oil, palm oil, palm kernel oil, soybean oil, rapeseed oil, cottonseed oil, olive oil, beef tallow, fish oil and the like.

Examples of the fatty acid include those constituting the above-described fatty acid esters and fatty acid triglycerides.

Among these starting materials, a fatty acid methyl ester is widely used.

Further, fractions of these fatty acid esters or fatty acids obtained, for example, by distillation may also be used.

As a pre-treatment of the hydrogenation, a treatment eliminating impurities from the fatty acid ester, fatty acid triglyceride or fatty acid may be conducted. Although a treatment of the starting material with a guard reactor which is located before the main reactor and contains a catalyst capable of eliminating the impurities is particularly preferred as the treatment, desulfurization, denitrification, dephosphorization and dehalogenation of the starting material through distillation or extraction may also be useful and these treatments may be conducted in combination.

In the treatment with the use of the guard reactor, the impurities are eliminated through a catalytic chemical reaction and/or adsorption. As the catalyst, Cu-series or Ni-series ones may be employed. Examples of the Cu-series catalyst include those exemplified for the hydrogenation catalyst. Examples of the Ni-series catalyst include those comprising Ni and conventionally used for the desulfurization of petroleum. Any reactors (for example, a fluidized bed reactor, a moving bed reactor, a fixed bed reactor) may be used therefor. Although the temperature and the flow rate of the starting material in the guard reactor may be determined based on the amount of impurities, which deteriorate the activity of the hydrogenation catalysts in the main and after reactors, in the starting material, the activity of the hydrogenation catalysts, the amount of the impurities to be eliminated from the starting material and the like, the temperature in the guard reactor is preferably controlled to 50° to 350° C., and the flow rate of the starting material in the guard reactor is preferably controlled so as to give a volume ratio to the reactor per hour (liquid hourly space velocity, hereinafter referred to as LHSV) of about 0.05 to about 20 1/hr, more preferably about 0.1 to about 10 1/hr, and furthermore preferably 0.2 to 5 1/hr. Most of the impurities (sulfur compounds may be cited as typical examples thereof) contained in a large amount in the starting fatty acid ester, fatty acid triglyceride or fatty acid can be eliminated by the treatment with the guard reactor. Thus the deterioration in the activity of the hydrogenation catalyst can be suppressed. In particular, when a fixed bed reactor is used as the main reactor and/or the after reactor, the life of the activity of the catalyst can be remarkably prolonged.

When a large amount of sulfur compounds should be eliminated by using a guard reactor, an excessively large volume of the reactor or frequent exchanges of the catalyst contained in the reactor is sometimes required for the guard reactor depending on the content of the sulfur compounds in the starting material.

In such a case, it is particularly effective to reduce the sulfur compounds in the starting material by distilling the starting material prior to it being fed into the guard reactor, followed by eliminating the sulfur compounds with the use of the guard reactor. Thus the active life of the catalyst contained in the guard reactor can be remarkably prolonged.

The hydrogenation may be effected by continuously catalytically reducing the starting material under a hydrogen pressure of from about 20 to about 300 bar in the presence of a hydrogenation catalyst in such a manner as to give a molar ratio of hydrogen to the fatty acid group of the starting material of from about 5:1 to about 500:1, preferably from about 10:1 to about 200:1, and more preferably from about 15:1 to about 100:1.

The flow rate of the starting material in the main and after reactors may vary depending on the kind of the hydrogenation catalyst, the activity of the hydrogenation catalyst, the reaction temperature, the molar ratio of hydrogen to the fatty acid group of the starting material and the kind of the starting material, and it is preferably controlled as to give an LHSV of about 0.05 to about 20 1/hr, more preferably about 0.1 to about 10 1/hr, and furthermore preferably about 0.2 to about 5 1/hr in either the fluidized bed, the moving bed or be fixed bed reactors.

The temperatures in the main and after reactors may vary depending on the type of the reactors, the kind of the hydrogenation catalyst, the activity of the hydrogenation catalyst, the molar ratio of hydrogen to the fatty acid group of the starting material and the kind and the flow rate of the starting material. In a typical case wherein both of the main and after reactors are fluidized bed ones, for example, the reaction temperature in the main reactor may range from 200° to 350° C., preferably from 240° to 300° C., and more preferably from 260° to 280° C., while the reaction temperature in the after reactor is lower than that in the main reactor and preferably controlled within a range of from 160° to 270° C., more preferably from 180° to 250° C., and furthermore preferably from 200° to 230° C. When fixed bed reactors or moving bed reactors are employed, the reaction temperature in the main reactor may range from 120° to 300° C., preferably from 160° to 270° C., and more preferably from 180° to 250° C., while the reaction temperature in the after reactor is lower than that in the main reactor and preferably controlled within a range of from 80° to 220° C., more preferably from 100° to 200° C., and furthermore preferably from 120° to 180° C. The hydrocarbon by-products concentration in the reaction products at the outlet of the main reactor is controlled to 0.5% by weight or less. Also, the conversion ratio at the outlet of the main reactor may preferably be controlled to from 50 to 100%, more preferably from 60 to 100%, furthermore preferably from 80 to 100%, and still furthermore preferably from 90 to 100%. When the conversion ratio at the outlet of the main reactor is smaller than 50% and the reaction temperature in the after reactor is relatively low to reduce the remaining starting material, an excessively large capacity is required for the after reactor. On the other hand, an excessively high reaction temperature in the after reactor may cause an undesirably large aldehyde formation.

The conversion ratio and the composition of the starting material and the reaction products in the reactors can be determined by analyzing the reaction system in the reactors. Alternately, it may easily be evaluated by a common calculation method, i.e., through the calculation of the material balance and the heat balance by taking the gas/liquid equilibrium, chemical reaction rate and the physicochemical phenomena in the reactor into consideration. Sampling of the reaction products can be conducted through sampling nozzles provided at positions in the vertical direction of the reactors, or at a transport line between the two reactors. An alcohol, a hydrocarbon, a fatty acid ester, a glyceride, a fatty acid and carbon monoxide in the reaction system can be analyzed by gas chromatography, while an aldehyde can be analyzed by a method according to JIS K 1525-1960 (the term "JIS" as used herein means "Japanese Industrial Standard") or in a manner as disclosed, for example, in A. S. Henick et al, *J. Am. Oil Chemists Socy.*, vol. 31, 88 (1954) and Shinji Mitsunaga et al, *Oil Chemistry*, vol. 7, (5), 275 (1958). The calculation method may be, for example, as in Shigeo Goto, *AIChE Journal*, vol. 21, No. 4, page 706 (1975); *ibid*, page 714; and Giorgio Soave, *Chemical Engineering Science*, vol. 27, pages 1197-1203 (1972).

Since the reduction of the fatty acid ester, fatty acid triglyceride or fatty acid is exothermic, it is preferable to control the temperature in each reactor by discharging the heat generated during the reaction in a known manner. For example, the control of the temperature in the reactors can be performed by a cooling means provided to the reactors. As the cooling means, either a direct cooling means using quench hydrogen, a quench oil or an inert quench substance, an indirect cooling means using a coolant, or a combination of the direct cooling means and the indirect cooling means may be employed in the present invention. Details of the cooling means may be, for example, as in Stanley M. Walas, *Chemical Process Equipment*, published by Butterworth publishers (1988); *Chemical Economy & Engineering Review*, vol 3, No. 9 (No. 41), pages 14-28 (1971); *Ind. Eng. Chem. Process Des. Dev.*, vol. 15, No. 3, pages 400-406 (1976); *Ind. Eng. Chem. Process Des. Dev.*, vol 17, No. 1, Page 27 et seq. (1978); Howard F. Rase, *CHEMICAL REACTOR DESIGN FOR PROCESS PLANTS*, volume two, pages 61-84 (1977). Positions and the number of the cooling means and the amount of quench hydrogen or the quench oil may be determined depending on the type of the reactor, the kind of the hydrogenation catalyst, the activity of the hydrogenation catalyst, the reaction temperature, the molar ratio of hydrogen to the fatty acid group of the starting material and the kind and flow rate of the starting material.

As described above, the concentrations of hydrocarbon and aldehyde by-products, which are formed during the process for producing a fatty alcohol, can be suppressed at an extremely low level by individually controlling the reaction temperature in each reactor. Namely, the hydrocarbon by-products can be reduced by precisely controlling the formation ratio of the alcohol, temperature and pressure. By controlling the temperature of the main reactor, the concentration of the hydrocarbons can be reduced to 0.5% by weight or less, preferably 0.3% weight or less and more preferably 0.1% by weight or less, based on the weight of the reaction products.

On the other hand, the aldehyde by-products can be converted into the corresponding alcohols by carrying out the reaction in the presence of a hydrogenation catalyst under a hydrogen atmosphere at a low temperature. By controlling the temperature of the after reactor, the concentration of the aldehydes can also be reduced to 30 ppm or less, preferably 10 ppm or less and more preferably 3 ppm or less. That is, in the after reactor, the reaction is carried out under a low temperature so as to suppress formation of the hydrocarbon by-products. When the temperature of the after reactor required to suppress the aldehyde by-products concentration at a desired level is too low to elevate the conversion ratio of the starting material, it is preferred that the temperature of the main reactor is elevated so as to increase the conversion ratio of the starting material in the main reactor. Such a temperature control makes it possible to obtain a desired conversion ratio of the starting material while keeping the aldehyde by-products concentration at a desired level. Carbon monoxide contained in the excessive hydrogen from the reactors exerts no undesirable effect on the qualities of the alcohol product. In a conventional method for producing an alcohol, this excessive hydrogen is recovered and reused. When the recovered hydrogen contains carbon monoxide, however, carbon monoxide would act as a poison to the employed hydrogenation catalyst and thus the catalytic activity is deteriorated thereby. This problem is particularly serious when fixed bed reactors are used. The concentration of the carbon monoxide in excess hydrogen at the outlet of the after reactor can be reduced to 1000 ppm or below by maintaining the temperature in the after reactor to 250° C. or below, since the carbon monoxide is converted into methanol when the reaction is carried out in the presence of a hydrogenation catalyst under a hydrogen atmosphere at such a low temperature. More preferably, the carbon monoxide concentration can be reduced to 200 ppm or less by maintaining the temperature in the after reactor at 200° C. or below, and, furthermore preferably, it can further be reduced to 10 ppm or less by maintaining the after reactor at 150° C. or below.

One of preferred embodiments of the present invention comprises transporting the reaction products from the main reactor to the after reactor, conducting gas/liquid separation under a high pressure hydrogen atmosphere and maintaining the hydrogenation catalyst in the case of the fluidized bed reactor or fixing the hydrogenation catalyst in the case of the fixed bed reactor in the liquid phase thus separated. This is a hydrogenation reaction with hydrogen dissolved in the liquid phase under high pressure, and it is expected to a highly useful embodiment depending on the type of the reactors and the capacity of the equipment.

To further illustrate the present invention, and not by way of limitation, the following Examples will be given.

In these Examples and Comparative Examples, the conversion ratio is defined as follows, when the starting material is a fatty acid ester or a fatty acid triglyceride:

Conversion Ratio (%) = $(1 - SV/SV_o) \times 100$ wherein SV means the saponification value of the reaction product and $SV_o$ means the saponification value of the starting material.

When the starting material is a fatty acid, the conversion ratio is defined as follows:

Conversion Ratio (%) = $(1 - AV/AV_o) \times 100$ wherein AV means the acid value of the reaction product and $AV_o$ means the acid value of the starting material.

EXAMPLE 1 AND COMPARATIVE EXAMPLE 1

Two reactors (inner diameter: 10 mm; height: 100 mm) were connected together and the temperature in each reactor was controlled with an external heater. An undistilled coconut oil methyl ester and 2.0% by weight, based on the methyl ester, of a marketed Cu-Cr powdery catalyst (N203, manufactured by NIKKI CHEMICAL Co., Ltd.) were fed thereto with hydrogen at 250 bar in ascending parallel flows to thereby perform a fluidized bed reaction. In Comparative Example 1, the same procedure was repeated except that a single reactor was employed.

Table 1 summarizes the reaction conditions and the analytical data of the obtained products.

TABLE 1

|  | Example 1 | Comparative Example 1 |
|---|---|---|
| Temperature in the main reactor (°C.) | 260 | 275 |
| Temperature in the after reactor (°C.) | 235 | — |
| Liquid hourly space velocity (LHSV) (1/hr) | 1 | 1 |
| Molar ratio of hydrogen to fatty acid group in the starting material | 15 | 15 |
| Main reactor outlet: | | |
| Outlet conversion ratio (%) | 80 | 99 |
| Hydrocarbon content (%) | 0.20 | 0.55 |
| Reaction product: | | |
| Conversion ratio (%) | 98.8 | 98.8 |
| Saponification value (KOH mg/mg) | 3 | 3 |
| Aldehyde concentration (ppm) | 20 | 100 |
| CO concentration (ppm) | 250 | 1500 |

The analytical data of the starting undistilled coconut oil methyl ester were as follows:
Saponification value: 255
Acid value: 0.1
Hydroxyl value: 4.5.

As Table 1 shows, the formation of the by-products was suppressed in Example 1, while a clearly larger amount of by-products was formed in Comparative Example 1.

EXAMPLE 2 AND COMPARATIVE EXAMPLE 2

By using the same reactors as those employed in Example 1, 20 cc portions of a marketed molded Cu-Cr catalyst (diameter: 3 mm) (N202D, manufactured by NIKKI CHEMICAL Co., Ltd.) were packed and an undistilled coconut oil methyl ester was continuously fed together with hydrogen at 250 bar in descending flow to thereby perform a fixed bed reaction. In Comparative Example 2, the same procedure was repeated except that a single reactor was employed.

Table 2 summarizes the reaction conditions and the analytical data of the obtained products.

TABLE 2

|  | Example 2 | Comparative Example 2 |
|---|---|---|
| Temperature in the main reactor (°C.) | 220 | 230 |
| Temperature in the after reactor (°C.) | 140 | — |
| Liquid hourly space velocity (LHSV) (1/hr) | 2 | 2 |
| Molar ratio of hydrogen to fatty acid group in the starting material | 60 | 60 |
| Main reactor outlet: | | |
| Outlet conversion ratio (%) | 90 | 99 |
| Hydrocarbon content (%) | 0.1 | 0.52 |
| Reaction product: | | |
| Conversion ratio (%) | 98.8 | 98.8 |
| Saponification value (KOH mg/mg) | 3 | 3 |
| Aldehyde concentration | 3 | 70 |

TABLE 2-continued

|  | Example 2 | Comparative Example 2 |
|---|---|---|
| (ppm) | | |
| CO concentration (ppm) | 2 | 250 |

The analytical data of the starting undistilled coconut oil methyl ester were as follows:
Saponification value: 255
Acid value: 0.1
Hydroxyl value: 0.1.

As Table 2 shows, the formation of the by-products was suppressed in Example 2, while a clearly larger amount of by-products was formed in Comparative Example 2.

EXAMPLE 3 AND COMPARATIVE EXAMPLE 3

By using the same reactors and the same catalyst as those employed in Example 2, an undistilled coconut oil was continuously fed together with hydrogen at 250 bar in descending flow to thereby perform a fixed bed reaction. In Comparative Example 3, the same procedure was repeated except that a single reactor was employed.

Table 3 summarizes the reaction conditions and the analytical data of the obtained products.

TABLE 3

|  | Example 3 | Comparative Example 3 |
|---|---|---|
| Temperature in the main reactor (°C.) | 200 | 220 |
| Temperature in the after reactor (°C.) | 150 | — |
| Liquid hourly space velocity (LHSV) (1/hr) | 0.5 | 0.5 |
| Molar ratio of hydrogen to fatty acid group in the starting material | 100 | 100 |
| Main reactor outlet: | | |
| Outlet conversion ratio (%) | 85 | 99 |
| Hydrocarbon content (%) | 0.43 | 0.60 |

TABLE 3-continued

|  | Example 3 | Comparative Example 3 |
|---|---|---|
| Reaction product: | | |
| Conversion ratio (%) | 99.4 | 99.4 |
| Saponification value (KOH mg/mg) | 1.5 | 1.5 |
| Aldehyde concentration (ppm) | 5 | 50 |
| CO concentration (ppm) | 3 | 60 |

The analytical data of the starting undistilled coconut oil were as follows:
Saponification value: 245
Acid value: 0.1
Hydroxyl value: 3.0.

As Table 3 shows, the formation of the by-products was suppressed in Example 3, while clearly larger amounts of hydrocarbons and aldehydes were formed in Comparative Example 3.

EXAMPLES 4 to 6 2 AND COMPARATIVE EXAMPLE 4

An undistilled or distilled coconut oil methyl ester was reduced with a hydrogen pressure of 250 bar in the same reactor as those employed in Example 2 and 3 (Example 4) or in a reactor wherein another reactor having the same size as other reactors and in which 20 cc of a marketed molded Ni catalyst (diameter: 3 mm) (C46, manufactured by Catalysts and Chemicals Ins., Far East) was packed was further located before the two reactors as a guard reactor in series (Examples 5 and 6). The operation were continuously performed for 1 month. In Comparative Example 4, the undistilled fatty acid methyl ester was continuously reduced in a main reactor alone without using any guard reactor or after reactor.

Table 4 summarizes the reaction conditions and the analytical data of the obtained products immediately after starting the reaction and after performed for 1 month running.

TABLE 4

|  | Example 4 | Example 5 | Example 6 | Comparative Example 4 |
|---|---|---|---|---|
| Starting material | Undistilled | Undistilled | Distilled | Undistilled |
| Temperature in the guard reactor | — | 150 | 150 | — |
| Temperature in the main reactor (°C.) | 200 | 200 | 200 | 220 |
| Temperature in the after reactor (°C.) | 150 | 150 | 150 | — |
| Liquid hourly space velocity (LHSV) (1/hr) | 1 | 1 | 1 | 1 |
| Molar ratio of hydrogen to fatty acid group in the starting material | 25 | 25 | 25 | 25 |

|  | Example 4 | | Example 5 | | Example 6 | | Comparative Example 4 | |
|---|---|---|---|---|---|---|---|---|
|  | A[1] | B[2] | A[1] | B[2] | A[1] | B[2] | A[1] | B[2] |
| Main reactor outlet: | | | | | | | | |
| Outlet conversion ratio (%) | 80 | 45 | 80 | 75 | 80 | 78 | 99 | 41 |
| Hydrocarbon content (%) | 0.03 | —[3] | 0.03 | 0.01 | 0.03 | 0.02 | 0.1 | —[3] |
| Reaction product: | | | | | | | | |
| Conversion ratio (%) | 98.8 | 60.8 | 98.8 | 96.1 | 98.8 | 98.0 | 98.8 | 41.2 |
| Saponification value (KOH mg/mg) | 3 | 100 | 3 | 10 | 3 | 5 | 5 | 150 |
| Aldehyde concentration (ppm) | 3 | —[3] | 3 | 3 | 3 | 3 | 35 | —[3] |

TABLE 4-continued

| | | | | | | | | |
|---|---|---|---|---|---|---|---|---|
| CO concentration (ppm) | 10 | 2 | 10 | 10 | 10 | 10 | 40 | —3) |

Notes:
1) Immediately after starting the reaction
2) After 1 month running
3) No by-product was formed due to high saponification value (low conversion ratio).

The analytical data of the starting undistilled coconut oil methyl ester and distilled coconut oil methyl ester were as follows:
Saponification value: 255
Acid value: 0.1
Hydroxyl value: 4.5.

As the data of Examples 4 to 6 and Comparative Example 4 given in Table 2 show, the increase in the saponification value after 1 month was suppressed by using the guard reactor.

EXAMPLE 7 AND COMPARATIVE EXAMPLE 5

By using the same reactors and the same catalyst as those employed in Examples 2, 3 and 4, a coconut oil fatty acid was continuously fed together with hydrogen at 250 bar in descending flow to thereby perform a fixed bed reaction.

In Comparative Example 5, the same procedure was repeated except that a single reactor was employed.

Table 5 summarizes the reaction conditions and the analytical data of the obtained products.

TABLE 5

| | Example 7 | Comparative Example 5 |
|---|---|---|
| Temperature in the main reactor (°C.) | 240 | 250 |
| Temperature in the after reactor (°C.) | 140 | — |
| Liquid hourly space velocity (LHSV) (1/hr) | 2 | 2 |
| Molar ratio of hydrogen to fatty acid group in the staring material | 60 | 60 |
| Main reactor outlet: | | |
| Outlet conversion ratio (%) | 95 | 99 |
| Hydrocarbon content (%) | 0.30 | 0.70 |
| Reaction product: | | |
| Conversion ratio (%) | 99.2 | 99.2 |
| Acid value (KOH mg/mg) | 2 | 2 |
| Aldehyde concentration (ppm) | 3 | 120 |
| CO concentration (ppm) | 3 | 500 |

The analytical data of the starting undistilled coconut oil fatty acid were as follows:
Acid value: 265
Iodine value: 8.5.

As Table 5 shows, the formation of the by-products was suppressed in Example 7, while a clearly larger amount of by-products was formed in Comparative Example 5.

Thus it can be understood that an alcohol having extremely good qualities and a high purity and contaminated with little hydrocarbon and aldehyde by-products can be produced in the process according to the present invention with the use of two reactors (i.e., the main reactor and the after reactor).

The process of the present invention further makes it possible to omit the post-treatment for eliminating the by-products.

Furthermore, the active life of the hydrogenation catalyst can be remarkably prolonged by using three reactors, i.e., the guard reactor, the main reactor and the after reactor.

While the invention has been described in detail and with reference to specific examples thereof, it will be apparent to one skilled in the art that various changes and modifications can be made therein without departing from the spirit and scope thereof.

What is claimed is:

1. A process for producing an alcohol which comprises:
   continuously feeding a starting material selected from the group consisting of a fatty acid ester and a fatty acid with hydrogen into two separate reactors which are located in series and in each of which a hydrogenation catalyst is contained, hydrogen being fed at about 20 to 300 bar and the starting material being fed in such a manner as to give a molar ratio of hydrogen to the fatty acid group of the starting material of from about 5:1 to about 500:1;
   reacting the starting material and hydrogen in the presence of the hydrogenation catalysts in said two separate reactors; and then
   recovering the alcohol,
   wherein said two separate reactors comprise a main reactor being located at the upstream and an after reactor being located at the downstream,
   a temperature of said main reactor is controlled so as to give a conversion ratio of the starting material at the outlet of said main reactor of 50 to 100% and a hydrocarbon by-product concentration of 0.5% by weight or less in reaction products at the outlet of said main reactor, and
   a temperature of said after reactor is controlled so as to elevate a conversion ratio of the starting material at the outlet of said main reactor and/or to give an aldehyde concentration in the reaction products at the outlet of said after reactor of 30 ppm or less and a carbon monoxide concentration in an excess hydrogen at the outlet of said after reactor is controlled to be 1,000 ppm or less, wherein said two reactors are both fluidized bed reactors where the temperature in the main reactor is 200° to 350° C. and the temperature in the after reactor is lower than the temperature in the main reactor and is 160° to 270° C. or wherein said two reactors are both fixed bed reactors where the temperature in the main reactor is 120° to 300° C. and the temperature in the after reactor is lower than the temperature in the main reactor and is 80° to 220° C.

2. A process of claim 1, wherein the main reactor is a fixed bed reactor and the temperature therein is 160° to 270° C. and the after reactor is a fixed bed reactor and the temperature therein is 100° to 200° C. or the main reactor is a fluidized bed reactor and the temperature therein is 240° to 300° C. and the after reactor is a fluidized bed reactor and the temperature therein is 180° to 250° C., and wherein said hydrocarbon by-product concentration in the reaction products at the outlet of said main reactor is controlled to be 0.3% by weight or less, the aldehyde by-product concentration in the reaction products at the outlet of said after reactor is controlled to be 10 ppm or less and a carbon monoxide concentration in an excess hydrogen at the outlet of said after reactor is controlled to be 200 ppm or less.

3. A process of claim 1, wherein the main reactor is a fixed bed reactor and the temperature therein is 180° to 250° C. and the after reactor is a fixed bed reactor and the temperature therein is 120° to 180° C. or the main reactor is fluidized bed reactor and the temperature therein is 260° to 280° C. and the after reactor is a fluidized bed reactor and the temperature therein is 200° to 230° C., and wherein said hydrocarbon by-product concentration in the reaction products at the outlet of said main reactor is controlled to be 0.1% by weight or less, the aldehyde by-product concentration in the reaction products at the outlet of said after reactor is controlled to be 3 ppm or less and a carbon monoxide concentration in an excess hydrogen at the outlet of said after reactor is controlled to be 10 ppm or less.

4. A process of claim 1, wherein said starting material is a fatty acid methyl ester.

5. A process of claim 1, wherein said hydrogenation catalyst in said main reactor is Cu-Zn-Ti catalyst.

6. A process of claim 1, wherein said hydrogenation catalyst in said main reactor is Cu-Fe-Al catalyst.

7. A process of claim 1, wherein said hydrogenation catalyst in said main reactor is Cu-Cr catalyst.

8. A process of claim 1, wherein said hydrogenation catalyst in said after reactor is Cu-Zn-Ti catalyst.

9. A process of claim 1, wherein said hydrogenation catalyst in said after reactor is Cu-Fe-Al catalyst.

10. A process of claim 1, wherein said hydrogenation catalyst in said after reactor is Cu-Cr catalyst.

11. A process of claim 1, wherein a guard reactor is further employed.

12. A process of claim 11, wherein said guard reactor contains a catalyst comprising Ni.

13. A process of claim 11, wherein each of said main reactor, after reactor and guard reactor is a fixed bed reactor.

14. A process of claim 4, wherein a guard reactor is further employed and each of said main reactor, after reactor and guard reactor is a fixed bed reactor.

15. A process of claim 1, wherein said fatty acid ester is a fatty acid triglyceride.

* * * * *